United States Patent
Carter et al.

(10) Patent No.: US 8,758,686 B2
(45) Date of Patent: Jun. 24, 2014

(54) OPTICAL CHEMICAL SENSING DEVICE WITH PYROELECTRIC OR PIEZOELECTRIC TRANSDUCER

(75) Inventors: Timothy Joseph Nicholas Carter, Ashford (GB); Steven Andrew Ross, Ashford (GB)

(73) Assignee: Vivacta Limited, Sittingbourne, Kent (GB)

( * ) Notice: Subject to any disclaimer, the term of this patent is extended or adjusted under 35 U.S.C. 154(b) by 1783 days.

(21) Appl. No.: 10/552,702

(22) PCT Filed: Apr. 8, 2004

(86) PCT No.: PCT/GB2004/001551
§ 371 (c)(1),
(2), (4) Date: Jul. 14, 2006

(87) PCT Pub. No.: WO2004/090512
PCT Pub. Date: Oct. 21, 2004

(65) Prior Publication Data
US 2006/0263894 A1    Nov. 23, 2006

(30) Foreign Application Priority Data
Apr. 10, 2003 (GB) .................................. 0308324.3

(51) Int. Cl.
*G01N 21/63* (2006.01)
*G01J 5/00* (2006.01)

(52) U.S. Cl.
CPC .. *G01N 21/63* (2013.01); *G01J 5/00* (2013.01)
USPC ...................................... 422/68.1; 250/338.3

(58) Field of Classification Search
CPC ................................... G01J 5/00; G01N 21/63
USPC ...................................... 250/338.3; 422/68.1
See application file for complete search history.

(56) References Cited

U.S. PATENT DOCUMENTS 5,048,969 A    9/1991    Deason et al.
5,357,111 A    10/1994    Vecht
(Continued)

FOREIGN PATENT DOCUMENTS

EP         0 049 918 A1      4/1982
FR         2 715 226 A1      7/1995
WO       WO 90/13017 A1   11/1990

OTHER PUBLICATIONS

Gibson, Ceri A., et al., "Kinetic factors in the response of piezo-optical chemical monitoring devices," *Sensors and Actuators B*, Aug. 31, 1998, pp. 238-243, vol. 51, No. 1-3. Elsevier.Sequoia S.A., Lausanne, Switzerland.

Visser, Eric P., et al., "Measurement of thermal diffusion in thin films using a modulated laser technique: Application to chemical-vapor-deposited diamond films," *Journal of Applied Physics*, Apr. 1, 1992, pp. 3238-3248, vol. 71, No. 7.

(Continued)

*Primary Examiner* — Paul Hyun
(74) *Attorney, Agent, or Firm* — Rothwell, Figg, Ernst & Manbeck, P.C.

(57) ABSTRACT

This invention relates to a device (1) for detecting energy generated by non-radiative decay generated in a substance (2) on irradiation with electromagnetic radiation. The device (1) comprises a radiation source (6) adapted to generate a series of pulses of electromagnetic radiation, a transducer (3) having a pyroelectric or piezoelectric element and electrodes (4, 5) which is capable of transducing the energy generated by the substance (2) into an electrical signal, and a detector (7) which is capable of detecting the electrical signal generated by the transducer (3). The detector (7) is adapted to determine the time delay between each pulse of electromagnetic radiation from the radiation source (6) and the generation of the electric signal. The device (1) has a wide applicability in the fields of assays and monitoring.

30 Claims, 7 Drawing Sheets

(56) References Cited

U.S. PATENT DOCUMENTS

| | | | |
|---|---|---|---|
| 5,622,868 A * | 4/1997 | Clarke et al. | 436/147 |
| 6,306,598 B1 * | 10/2001 | Charych et al. | 435/6 |
| 6,403,944 B1 | 6/2002 | MacKenzie et al. | |
| 7,244,572 B1 * | 7/2007 | Schwabacher et al. | 435/7.1 |
| 2003/0005771 A1 * | 1/2003 | Percin et al. | 73/627 |

OTHER PUBLICATIONS

Wright, John D., et al., "Development of a piezo-optical chemical monitoring system," *Sensors and Actuators B*, Aug. 31, 1998, pp. 121-130, vol. 51, No. 1-3. Elsevier.Sequoia S.A., Lausanne, Switzerland.

\* cited by examiner

OPTICAL CHEMICAL SENSING DEVICE WITH PYROELECTRIC OR PIEZOELECTRIC TRANSDUCER

This application is a 371 filing of PCT/GB2004/001551, filed Apr. 8, 2004, which claims priority from GB Patent Application 0308324.3, filed Apr. 10, 2003.

The present invention relates to a chemical sensing device and in particular to a chemical sensing device employing a transducer.

The monitoring of analytes in solution, such as biologically important compounds in bioassays, has a broad applicability. Accordingly, a wide variety of analytical and diagnostic devices are available. Many devices employ a reagent which undergoes an eye-detectable colour change in the presence of the species being detected. The reagent is often carried on a test strip and optics may be provided to assist in the measurement of the colour change.

WO 90/13017 discloses a pyroelectric or other thermoelectric transducer element in a strip form. Thin film electrodes are provided and one or more reagents are deposited on the transducer surface. The reagent undergoes a selective calorimetric change when it comes into contact with the species being detected. The device is then typically inserted into a detector where the transducer is illuminated usually from below by an LED light source and light absorption by the reagent is detected as microscopic heating at the transducer surface. The electrical signal output from the transducer is processed to derive the concentration of the species being detected.

The system of WO 90/13017 provides for the analysis of species which produce a colour change in the reagent on reaction or combination with the reagent. For example, reagents include pH and heavy metal indicator dyes, reagents (e.g. o-cresol in ammoniacal copper solution) for detecting aminophenol in a paracetamol assay, and a tetrazolium dye for detecting an oxidoreductase enzyme in an enzyme-linked immuno-sorbant assay (ELISA). However, while this system is useful in certain applications, it has been considered suitable only for analysis where the species being analysed generates a colour change in the reagent since it is the reagent which is located on the surface of the transducer. Therefore, this system cannot be applied to the analysis of species which do not cause a colour change in the reagent or when the colour change is not on the surface of the transducer. In the field of bioassays, this gives the system limited applicability.

Accordingly, the present invention provides a device for detecting energy generated by non-radiative decay in a substance on irradiation with electromagnetic radiation comprising a radiation source adapted to generate a series of pulses of electromagnetic radiation, a transducer having a pyroelectric or piezoelectric element and electrodes which is capable of transducing the energy generated by the substance into an electrical signal, and a detector which is capable of detecting the electrical signal generated by the transducer, wherein the detector is adapted to determine the time delay between each pulse of electromagnetic radiation from the radiation source and the generation of the electric signal.

The present invention relies on the finding by the applicant that energy, typically heat, generated by non-radiative decay in a substance on irradiation with electromagnetic radiation, herein termed "light", may be detected by a transducer even when the substance is not in contact with the transducer and moreover, that the time delay between the irradiation with electromagnetic radiation and the electrical signal produced by the transducer is a function of the distance of the substance from the surface of the film. This finding has a wide applicability in the fields of assays and monitoring.

The present invention also provides a method for detecting energy generated by non-radiative decay in a substance on irradiation with electromagnetic radiation, comprising the steps of irradiating the substance with a series of pulses of electromagnetic radiation to generate energy, transducing the change in energy to an electrical signal using a transducer having a pyroelectric or piezoelectric element and electrodes which is capable of transducing a change in energy to an electrical signal, detecting the electrical signal generated by the transducer, and determining the time delay between each pulse of electromagnetic radiation from the radiation source and the generation of the electric signal.

The present invention will now be described with reference to the drawings, in which FIG. 1 shows a schematic representation of the chemical sensing device of the present invention;

Figure 1:
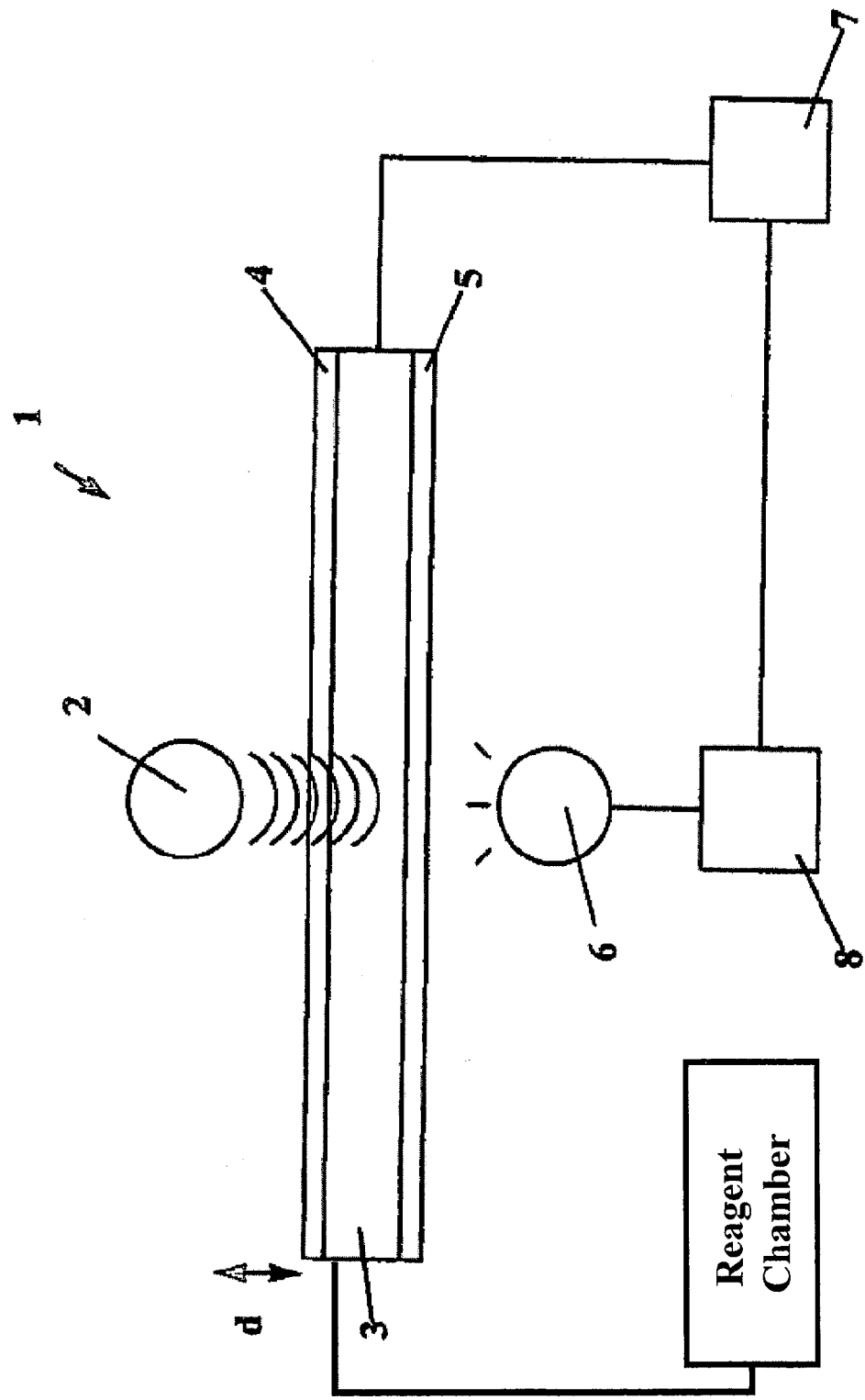

FIG. 1 shows a chemical sensing device 1 in accordance with the present invention which relies on heat generation in a substance 2 on irradiation of the substance 2 with electromagnetic radiation. FIG. 1 shows the chemical sensing device 1 in the presence of a substance 2. The device 1 comprises a pyroelectric or piezoelectric transducer 3 having electrode coatings 4,5. The transducer 3 is preferably a poled polyvinylidene fluoride film. The electrode coatings 4,5 are preferably formed from indium tin oxide having a thickness of about 35 nm, although almost any thickness is possible from a lower limit of 1 nm below which the electrical conductivity is too low and an upper limit of 100 nm above which the optical transmission is too low (it should not be less than 95% T). A substance 2 is held proximal to the piezoelectric transducer 3 using any suitable technique, shown here attached to the upper electrode coating 4. The substance may be in any suitable form and a plurality of substances may be deposited. Preferably, the substance 2 is adsorbed on to the upper electrode, e.g. covalently coupled or bound via intermolecular forces such as ionic bonds, hydrogen bonding or van der Waal's forces. A key feature of the present invention is that the substance 2 generates heat when irradiated by a source of electromagnetic radiation 6, such as light, preferably visible light. The light source may be, for example, an LED. The light source 6 illuminates the substance 2 with light of the appropriate wavelength (e.g. a complementary colour). Although not wishing to be bound by theory, it is believed that the substance 2 absorbs the light to generate an excited state which then undergoes non-radiative decay thereby generating energy, indicated by the curved lines in FIG. 1. This energy is primarily in the form of heat (i.e. thermal motion in the environment) although other forms of energy, e.g. a shock wave, may also be generated. The energy is, however, detected by the transducer and converted into an electrical signal. The device of the present invention is calibrated for the particular substance being measured and hence the precise form of the energy generated by the non-radiative decay does not need to be determined. Unless otherwise specified the term "heat" is used herein to mean the energy generated by non-radiative decay. The light source 6 is positioned so as to illuminate the substance 2. Preferably, the light source 6 is positioned below the transducer 3 and electrodes 4,5 and the substance 2 is illuminated through the transducer 3 and electrodes 4,5. The light source may be an internal light source within the transducer in which the light source is a guided wave system. The wave guide may be the transducer itself or the wave guide may be an additional layer attached to the transducer.

The energy generated by the substance 2 is detected by the transducer 3 and converted into an electrical signal. The electrical signal is detected by a detector 7. The light source 6 and the detector 7 are both under the control of the controller 8. The light source 6 generates a series of pulses of light (the term "light" used herein means any form of electromagnetic radiation unless a specific wavelength is mentioned) which is termed "chopped light". In principle, a single flash of light, i.e. one pulse of electromagnetic radiation, would suffice to generate a signal from the transducer 3. However, in order to obtain a reproducible signal, a plurality of flashes of light are used which in practice requires chopped light. The frequency at which the pulses of electromagnetic radiation are applied may be varied. At the lower limit, the time delay between the pulses must be sufficient for the time delay between each pulse and the generation of an electrical signal to be determined. At the upper limit, the time delay between each pulse must not be so large that the period taken to record the data becomes unreasonably extended. Preferably, the frequency of the pulses is from 2-50 Hz, more preferably 5-15 Hz and most preferably 10 Hz. This corresponds to a time delay between pulses of 20-500 ms, 66-200 ms and 100 ms, respectively. In addition, the so-called "mark-space" ratio, i.e. the ratio of on signal to off signal is preferably one although other ratios may be used without deleterious effect Sources of electromagnetic radiation which produce chopped light with different frequencies of chopping or different mark-space ratios are known in the art. The detector 7 determines the time delay (or "correlation delay") between each pulse of light from light source 6 and the corresponding electrical signal detected by detector 7 from transducer 3. The applicant has found that this time delay is a function of the distance, d.

Any method for determining the time delay between each pulse of light and the corresponding electrical signal which provides reproducible results may be used. Preferably, the time delay is measured from the start of each pulse of light to the point at which a maximum in the electrical signal corresponding to the absorption of heat is detected as by detector 7.

The finding that the substance 2 may be separated from the transducer surface and that a signal may still be detected is surprising since the skilled person would have expected the heat to be dispersed into the surrounding medium and hence be undetectable by the transducer 3 or at least for no meaningful signal to be received by the transducer. The applicant has found, surprisingly, that not only is the signal detectable through an intervening medium capable of transmitting energy to the transducer 3, but that different distances, d, may be distinguished (this has been termed "depth profiling") and that the intensity of the signal received is proportional to the concentration of the substance 2 at the particular distance, d, from the surface of the transducer 3. Moreover, the applicant has found that the nature of the medium itself influences the time delay and the magnitude of the signal at a given time delay. These findings provide a wide number of new applications for chemical sensing devices employing a transducer.

In one embodiment, the present invention provides a device as defined above wherein the substance is an analyte or a complex or derivative of the analyte, the device being used for detecting the analyte in a sample, the device further comprising at least one reagent proximal to the transducer, the reagent having a binding site which is capable of binding the analyte or the complex or derivative of the analyte, wherein the analyte or the complex or derivative of the analyte is capable of absorbing the electromagnetic radiation generated by the radiation source to generate heat, wherein, in use, the heat generated is transduced into an electrical signal by the transducer and is detected by the detector, and the time delay between each of the pulses of electromagnetic radiation and the generation of the electric signal corresponds to the position of the analyte at any of one or more positions at different distances from the surface of the transducer. The present invention also provides a method for detecting an analyte in a sample, comprising the steps of exposing the sample to a transducer having a pyroelectric or piezoelectric element and electrodes which is capable of transducing a change in heat to an electrical signal, the transducer having at least one reagent proximal thereto, the reagent having a binding site which is capable of binding the analyte or a complex or derivative of the analyte, the analyte or the complex or derivative of the analyte being capable of absorbing the electromagnetic radiation generated by the radiation source to generate heat; irradiating the reagent with a series of pulses of electromagnetic radiation, transducing the heat generated into an electrical signal; detecting the electrical signal and the time delay between each pulse of electromagnetic radiation from the radiation source and the generation of the electric signal, wherein the time delay between each of the pulses of electromagnetic radiation and the generation of the electric signal corresponds to the position of the analyte at any of one or more positions at different distances from the surface of the transducer. Such a device and method have applicability in, for example, immunoassays and nucleic acid—based assays. In a preferred example of an immunoassay, the reagent is an antibody and the analyte is an antigen.

In a typical immunoassay, an antibody specific for an antigen of interest is attached to a polymeric support such as a sheet of polyvinylchloride or polystyrene. A drop of cell extract or a sample of serum or urine is laid on the sheet, which is washed after formation of the antibody-antigen complex. Antibody specific for a different site on the antigen is then added, and the sheet is again washed. This second antibody carries a label so that it can be detected with high sensitivity. The amount of second antibody bound to the sheet is proportional to the quantity of antigen in the sample. This assay and other variations on this type of assay are well known, see, for example, "The Immunoassay Handbook, 2nd Ed." David Wild, Ed., Nature Publishing Group, 2001. The device of the present invention may be used in any of these assays.

Figure 2:
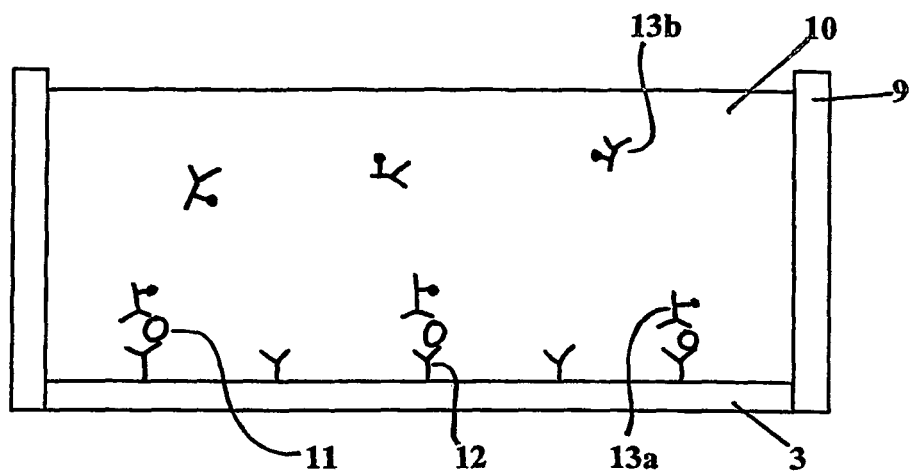
FIG. 2 shows a sandwich immunoassay using the device of the present invention.

By way of example, FIG. 2 shows a typical capture antibody assay using the device of the present invention. A device includes a transducer 3 and a well 9 for holding a liquid 10 containing an analyte 11 dissolved or suspended therein. The transducer 3 has a number of reagents, i.e. antibody 12, attached thereto. The antibody 12 is shown attached to the film in FIG. 2 and this attachment may be via a covalent bond or by non-covalent adsorption onto the surface, such as by hydrogen bonding. Although the antibody is shown as attached to the transducer, any technique for holding the antibody 12 proximal to the transducer 3 is applicable. For example, an additional layer may separate the antibody 12 and the transducer 3, such as a silicone polymer layer, or the antibody could be attached to inert particles and the inert particles are then attached to the transducer 3. Alternatively, the antibody 12 could be entrapped within a gel layer which is coated onto the surface of the transducer 3.

In use, the well is filled with liquid 10 (or any fluid) containing an antigen 11. The antigen 11 then binds to antibody 12. Additional labelled antibody 13 is added to the liquid and a so-called "sandwich" complex is formed between the bound antibody 12, the antigen 11 and the labelled antibody 13. An excess of labelled antibody 13 is added so that all of the bound antigen 11 forms a sandwich complex. The sample therefore contains bound labelled antigen 13a and unbound labelled antigen 13b free in solution.

During or following formation of the sandwich complex, the sample is irradiated using a series of pulses of electromagnetic radiation, such as light. The time delay between each pulse and the generation of an electrical signal by the transducer 3 is detected by a detector. The appropriate time delay is selected to measure only the heat generated by the bound labelled antigen 13a. Since the time delay is a function of the distance of the label from the transducer 3, the bound labelled antibody 13a may be distinguished from the unbound labelled antigen 13b. This provides a significant advantage over the conventional sandwich immunoassay in that it removes the need for washing steps. In a conventional sandwich immunoassay, the unbound labelled antibody must be separated from the bound labelled antibody before any measurement is taken since the unbound labelled antigen interferes with the signal generated by the bound labelled antigen. However, on account of the "depth profiling" provided by the present invention, bound and unbound labelled antigen may be distinguished. Indeed, the ability to distinguish between substances proximal to the transducer and substances in the bulk solution is a particular advantage of the present invention.

The labelled antibody is preferably labelled with a label selected from a dye molecule, a gold particle, a coloured polymer particle (e.g. a coloured latex particle), a fluorescent molecule, an enzyme, a red blood cell, a haemoglobin molecule, a magnetic particle and a carbon particle. However, any label capable of interacting with electromagnetic radiation to generate heat would be acceptable. In the case of a magnetic particle, the electromagnetic radiation is radio frequency radiation. All of the other labels mentioned hereinabove employ light. In the case of a gold particle, the label is enhanced using a solution of silver ions and a reducing agent. The gold catalyses/activates the reduction of the silver ions to silver metal and it is the silver metal which absorbs the light. All of these labels are conventional.

The labelled antibody, or indeed any one or more additional reagents are preferably stored in a chamber incorporated into the device of the present invention.

The antigen is typically a protein, such as a protein-based hormone, although smaller molecules, such as drugs, may be detected. The antigen may also be part of a larger particle, such as a virus, a bacterium, a cell (e.g. a red blood cell) or a prion.

As a further example of known immunoassays, the present invention may be applied to competitive assays in which the electrical signal detected by the detector is inversely proportional to the presence of an unlabelled antigen in the sample. In this case, it is the amount of the unlabelled antigen in the sample which is of interest.

In a competitive immunoassay, an antibody is attached to the transducer as shown in FIG. 2. A sample containing the antigen is then added. However, rather than adding a labelled antibody, a known amount of labelled antigen is added to the solution. The labelled and unlabelled antigens then compete for binding to the antibodies attached to the transducer 3. The concentration of the bound labelled antigen is then inversely proportional to the concentration of bound unlabelled antigen and hence, since the amount of labelled antigen is known, the amount of unlabelled antigen in the initial solution may be calculated. The same labels specified with reference to the antibodies may also be used with the antigens.

In an embodiment of the present invention, the analyte being detected may be present in a sample of whole blood. In many conventional assays, the presence of other components of the blood in solution or suspension, such as red blood cells, interferes with the detection of the particular analyte of interest. However, in the device of the present invention, since only the signal at a known distance from the transducer 3 is determined, the other components of the blood which are free in solution or suspension do not interfere with the detection. This simplifies the analysis of a blood sample since a separate separation step is not required. An apparatus for measuring analyte levels in a blood sample preferably comprises a hand-held portable reader and a disposable device containing the piezoelectric film. A small sample of blood (about 10 microlitres) is obtained and transferred to a chamber within the disposable device. One side of the chamber is made from the piezoelectric film coated with an antibody capable of binding to the analyte of interest. An additional solution may then be added containing, for example, labelled antibody or a known concentration of labelled antigen as described above. The reaction is allowed to proceed and the disposable device is then inserted into the reader which activates the measurement process. The results of the assay are then indicated on a display on the reader. The disposable device containing the piezoelectric film is then removed and discarded.

A potential source of background interference is the settling of suspended particles on to the surface of the pyroelectric or piezoelectric transducer. For example, this might occur in some devices using the generation of silver particles. This source of interference may be avoided by positioning the transducer above the bulk solution, e.g. on the upper surface of the reaction chamber. Thus, if any settling occurs, it will not interfere with the transducer. Alternatively, the particles could be less dense than the medium and hence float to the surface of the bulk solution rather than settling on the surface of the transducer. This and other modifications are included in the scope of the present invention.

In another embodiment, the device of the present invention is applied to lateral-flow analysis. This has particular application for the detection of human chorionic gonadotrophin (HCG) in pregnancy testing.

Figure 3:
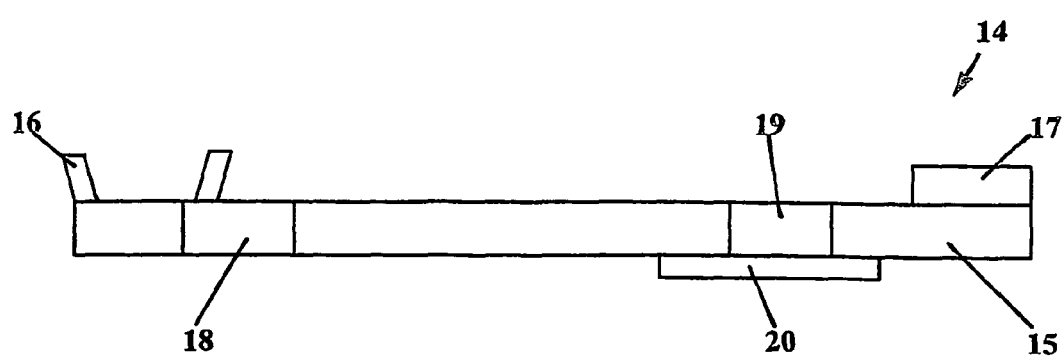
FIG. 3 shows a lateral-flow assay device in accordance with the present invention.

FIG. 3 shows a simplified lateral flow device 14 in accordance with the present invention. The device has a filter paper or other absorber 15 containing a sample receiver 16 and a wick 17 together with first and second zones 18 and 19 containing unbound and bound antibodies (i.e. unbound and bound to the filter paper or other absorber 15), respectively, capable of binding to HCG. The device also contains a piezoelectric film 20 proximal to the second zone 19. A sample of urine or serum is added to the sample receiver 16 which then travels along the absorber 15 to the wick 17. The first zone 18 contains a labelled antibody to HCG and as the sample passes through the first zone 18, if HCG is present in the sample, the labelled antibody to HCG is picked up by the sample. As the sample passes from the first zone 18 to the second zone 19, the antigen and antibody form a complex. At the second zone 19, a second antibody is attached either to the absorber 15 or the piezoelectric film 20 which is capable of binding the antigen-antibody complex. In a conventional lateral-flow analysis such as a pregnancy tester, a positive result produces a colour change at the second zone 19. However, the conventional lateral-flow analysis is restricted to clear samples and is essentially suitable only for a positive or negative i.e. yes/no, result. The device of the present invention, however, uses a piezoelectric film 20. Since only the sample at the predetermined distance from the film is measured, contaminants in the bulk sample will not affect the reading. Moreover, the sensitivity of the piezoelectric film provides a quantification of the result. Quantification of the result provides a broader applicability to the lateral-flow analysis and also distinguishing between different quantities of antigens reduces the number of erroneous results.

The device of the present invention is not restricted to detecting only one analyte in solution. Since the device provides "depth profiling" different analytes may be detected by employing reagents which selectively bind each analyte being detected wherein the reagents are different distances from the surface of the transducer 3. For example, two analytes may be detected using two reagents, the first reagent being positioned at a first distance from the film and the second reagent being positioned at a second distance from the film. The time delay between each pulse of electromagnetic radiation and the generation of electrical signal will be different for the two analytes bound to the first and second reagents.

As well as providing different depths, multiple tests may be carried out using different types of reagents, e.g. different antibodies, at different parts of the transducer. Alternatively, or in addition, multiple tests may be carried out using reagents/analytes which respond to different wavelengths of electromagnetic radiation.

The substance generating the heat may be on the surface of the film, however, preferably the substance is at least 5 nm from the surface of the film and, preferably, the substance is no more than 500 µm from the surface of the film. By selecting a suitable time delay, however, a substance in the bulk solution may also be measured.

As alternatives to antibody-antigen reactions, the reagent and analyte may be a first and second nucleic acid where the first and second nucleic acids are complementary, or a reagent containing avidin or derivatives thereof and an analyte containing biotin or derivatives thereof, or vice versa. The system is also not limited to biological assays and may be applied, for example, to the detection of heavy metals in water. The system also need not be limited to liquids and any fluid system may be used, e.g. the detection of enzymes, cells and viruses etc. in the air.

As described hereinabove, the applicant has found that the time delay between each pulse of electromagnetic radiation in the generation of an electric signal in the transducer is proportional to the distance of the substance from the film. Moreover, the applicant has found that the time delay depends on the nature of the medium itself.

Initially, it was surprising that a liquid medium does not totally dampen the signal. However, the applicant has found that changes in the nature of the medium can alter the time delay (i.e. until signal maximum is reached), the magnitude of the signal and the waveform of the signal (i.e. the variation of response over time).

These changes in the nature of the medium may be due to, amongst other things variations in the thickness of the medium, the elasticity of the medium, the hardness of the medium, the density of the medium, the deformability of the medium, the heat capacity of the medium or the speed at which sound/shock waves may be propagated through the medium.

The variation in time delay depending on the nature of the medium may, in itself, provide for useful applications. For example, the device of the present invention may be used to determine the progress of a chemical reaction, such as a polymerisation or depolymerisation reaction. A device of the present invention is as described above further comprising at least one substance proximal to the transducer, the substance being capable of absorbing the electromagnetic radiation generated by the radiation source to generate heat, wherein, in use, the heat generated is transduced into an electrical signal by the transducer and is detected by the detector, and the time delay between each of the pulses of electromagnetic radiation and the generation of the electric signal and/or the magnitude of the signal at a specific time delay, preferably a non-zero time delay, varies as the reaction progresses.

The present invention also provides a method for monitoring the progress of a reaction comprising the steps of exposing reactants in a reaction medium to a transducer having a pyroelectric or piezoelectric element and electrodes which is capable of transducing a change in heat to an electrical signal, the transducer having at least one substance proximal to the transducer, the substance being capable of absorbing the electromagnetic radiation generated by the radiation source to generate heat, irradiating the substance with a series of pulses of electromagnetic radiation, transducing the heat generated into an electrical signal; detecting the electrical signal and the time delay between each pulse of electromagnetic radiation from the radiation source and the generation of the electric signal, wherein the time delay between each of the pulses of electromagnetic radiation and the generation of the electric signal and/or the magnitude of the signal at a specific time delay varies as the reaction progresses.

EXAMPLES

A poled polyvinylidene fluoride bimorph, coated in indium tin oxide, was used as the sensing device in the following examples.

In Examples 1-4 and Comparative examples 1-3, the sensing device was dip-coated in polystyrene solution to give a polystyrene layer on top of the indium tin oxide. Circular polystyrene "washers" of internal diameter 5 mm and height 5 mm were attached to the polystyrene surface (using pressure sensitive adhesive) to form reaction wells, which could effectively constrain liquids above the surface of the sensing device. The wells hold a total volume of up to 100 µL of liquid. The polystyrene washers had been treated with a solution of bovine serum albumin (BSA) and Tween (RM) 20 (polyoxyethylene sorbitan monolaurate) to prevent non-specific binding of protein molecules to the walls of the reaction well.

Example 1

Figure 4:
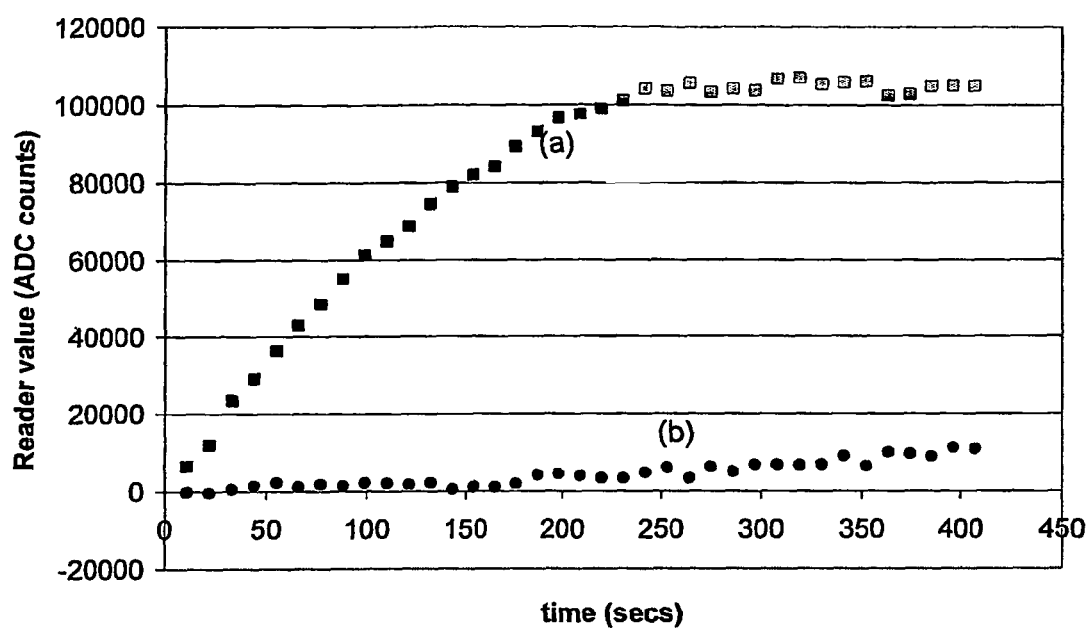
FIG. 4 shows a graph of reader value against time for (a) a labelled antibody on a piezoelectric film and (b) a labelled antibody in solution, both being enhanced by catalytic deposition of metallic silver.

FIG. 4 shows the results of two proof-of-principle experiments which detect the presence of (a) a labelled antibody attached to a piezoelectric film and (b) a labelled antibody in solution. The two experiments were carried out in reaction wells on the surface of polystyrene-coated piezoelectric film. In the first experiment (a) 50 µL of gold-labelled anti-horseradish peroxidase (HRP) solution (5 µg/mL, 250 ng total) in phosphate buffer (pH 7.2, 100 mM) were added to the reaction well and incubated for 1 hour, then rinsed off and dried. In the second experiment (b) the surface of the polystyrene film was blocked by incubation with a solution of bovine serum albumin (1%) and Tween (RTM) 20 (0.5%), then rinsed off and dried.

50 µL of premixed silver-enhancer solution (Sigma SE-100) was added to the first reaction well to initiate the enhancement reaction. 50 µL of premixed silver enhancer solution containing 250 ng of gold-labelled anti-HRP was added to the second well to initiate the enhancement reaction.

The wells were then irradiated with chopped light of wavelength 654 nm with a chopping frequency of 10 Hz. The magnitude of the maximum signal detected by the piezoelectric film at a correlation delay of around 10-15 ms was measured. The signal was displayed on an analogue-to-digital converter. FIG. 4 shows the results of these enhancement reactions. The y axis shows the signal received by the detector, termed "Reader value (ADC counts)" and the x axis shows time in seconds.

In the first experiment (a), the gold-labelled anti-HRP bound to the surface mediates the reaction between silver ions and reducing agent at the surface of the film, leading to deposition of metallic silver on to the transducer surface. In the second experiment (b), the gold-labelled anti-HRP in solution mediates the reaction between silver ions and reducing agent in solution, leading to the precipitation of silver particles. The kinetic profile of these reactions can be monitored over time, with measurements being taken every 10 seconds. Since the bulk solution is at a greater distance from the piezoelectric film than the bound label, little or no signal is detected at a correlation delay of around 10-15 ms. The quantities of anti-HRP used ensure that the quantity of anti-HRP on the surface in the first experiment (a) must be equal to or less than the quantity of anti-HRP in solution in the second experiment (b).

Incidentally, if a signal were detected at a correlation delay around 50-60 ms, the signal for the antibody in bulk solution would be measured rather than the bound antibody on the surface of the transducer, although because of the damping of the signal by the medium, the strength of the signal may be reduced.

Example 2

30 µL of a 1:30 dilution in 100 mM phosphate buffer, pH 7.2 of rabbit anti-horseradish peroxidase (HRP) immunoglobulin G (Sigma cat. No P7899) (IgG) was incubated in the reaction well for one hour at room temperature to allow adsorption of antibody onto the surface of the polystyrene. The solution was then rinsed off and treated with bovine serum albumin (1%) and Tween (RTM) 20 (0.05%) in a phosphate buffer (30 µL) to block any remaining adsorption sites on the polystyrene surface. The well was rinsed with deionised water and dried. 30 µL of horseradish peroxidase solution (125 µg/L in 100 mM phosphate buffer) was then added to the reaction well and incubated for 1 hour then rinsed off. 30 µL of gold-labelled goat (Fab')$_2$ anti-horseradish peroxidase (British Biocell) (1:10 dilution in 100 mM phosphate buffer) was added for one hour at room temperature. The well was then rinsed with deionised water. Silver enhancer solution (Sigma SE-100, consisting of 20 µL solution A and 20 solution B, which were premixed immediately prior to use) was then added to the reaction well and the development of metallic silver stain on the surface of the sensor was monitored by illumination of the sensor film using chopped light (10 Hz) from a high-energy blue LED (emitting at 470 nm). A voltage is generated across the sensor which is measured using a lock-in amplifier, then converted to an arbitrary digital signal and stored on a PC.

Comparative Example 1

The reaction was carried out exactly as described in Example 2 above, except that the initial step of adsorbing rabbit anti-HRP onto the surface of the sensor was omitted.

Comparative Example 2

The reaction was carried out exactly as described in Example 2 above, except that the incubation step with horseradish peroxidase was omitted.

Comparative Example 3

The reaction was carried out exactly as described above in Example 2, except that the incubation step with the gold-labelled goat (Fab')$_2$ anti-horseradish peroxidase antibody was omitted.

Figure 5:
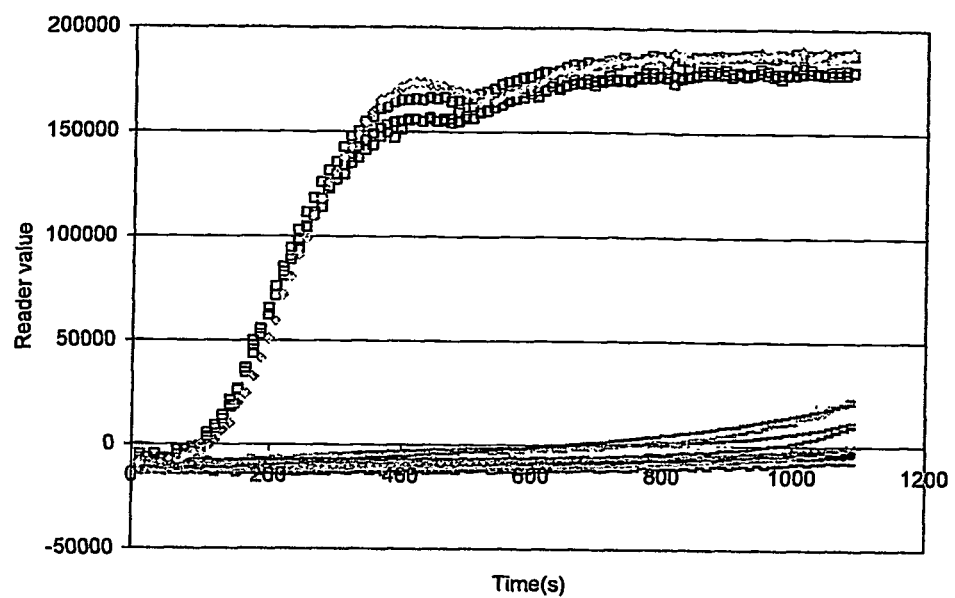
FIG. 5 shows the results of a sandwich assay using a colloidal gold-labelled antibody being enhanced by catalytic deposition of metallic silver on the surface of the piezoelectric film.

FIG. 5 shows the results from Example 2 and Comparative examples 1 to 3 (4 runs of each). The four data series which give rise to a rapid signal are due to the rabbit anti-HRP/HRP/gold-labelled goat anti-HRP sandwich on the surface of the sensor (Example 2). All other data series are due to control reactions (Comparative examples 1 to 3).

Example 3

Rabbit anti-horseradish peroxidase (HRP) immunoglobulin G (Sigma cat. No P7899) (IgG) (30 µL of a 1:30 dilution in 100 mM phosphate buffer, pH 7.2) was incubated in two reaction wells for one hour at room temperature to allow adsorption of antibody onto the surface of the polystyrene. The solutions were then rinsed off and treated with bovine serum albumin (1%) and Tween (RTM) 20 (0.05%) in phosphate buffer (30 µL) to block any remaining adsorption sites on the polystyrene surface. The wells were rinsed with deionised water and dried. 10 µL of horseradish peroxidase solution (125 µg/mL in 100 mM phosphate buffer) was then added to reaction well 1, whereas 10 µL of phosphate buffer alone was added to reaction well 2. These were left for 15 mins to incubate, then 30 µL of gold-labelled goat (Fab')$_2$ anti-horseradish peroxidase (British Biocell) (1:10 dilution in 100 mM phosphate buffer) was added to both wells 1 and 2 for 15 mins at room temperature. Silver enhancer solution (Sigma SE-100, consisting of 20 µL solution A and 20 solution B, which were premixed immediately prior to use) was then added to both reaction wells and the development of metallic silver stain on the surface of the sensor was monitored using the technique described previously.

The presence of HRP in well 1 as a model analyte, allows formation of a sandwich complex on the surface of the transducer (rabbit anti-HRP/HRP/gold-labelled goat anti-HRP), thus localising some of the gold label onto the surface in well 1. The absence of HRP in well 2 means that the gold-labelled goat antibody remains in solution in well 2.

The development of signal over time for wells 1 and 2 was similar to that presented in FIG. 4, illustrating that detection of analyte can take place without washing steps.

Example 4

Figure 6:
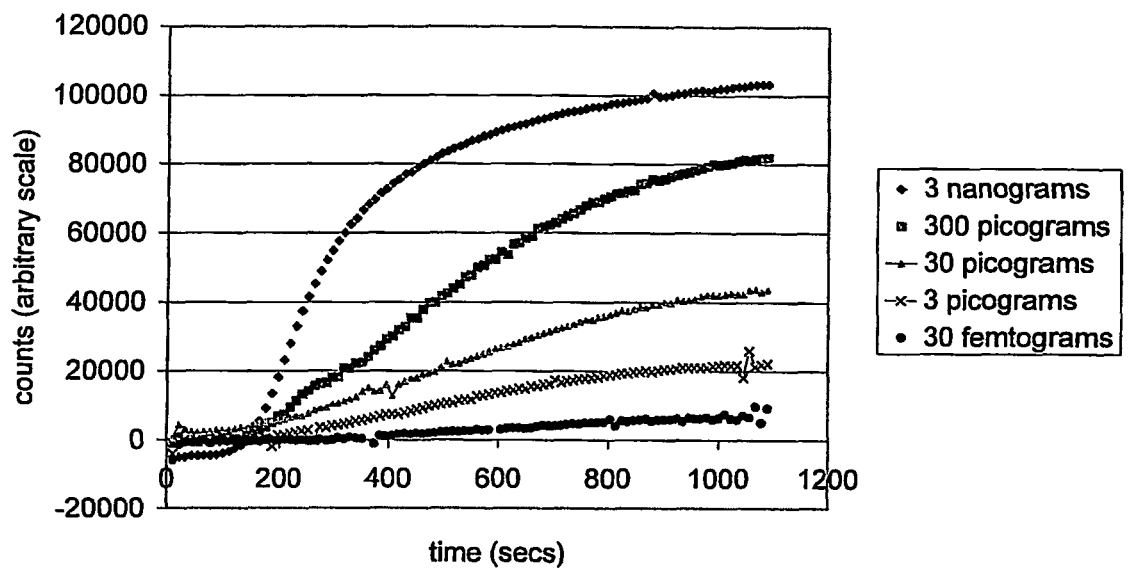
FIG. 6 shows the results of a sandwich assay using a gold-labelled antibody followed by catalytic deposition of metallic silver on the surface of the piezoelectric film using five different analyte concentrations.

A series of experiments were carried out exactly as described in Example 2, using rabbit anti-HRP IgG adsorbed onto the surface of the transducer as the capture antibody, HRP as the target analyte and gold-labelled goat anti-HRP IgG as the reporter antibody. Five different HRP concentrations were used (100 ng/mL, 10 ng/mL, 1 ng/mL, 100 pg/mL and 1 pg/mL)). This corresponded to total quantities of HRP equal to 3 ng, 300 pg, 30 pg, 3 pg and 30 fg. The silver-enhancement step was carried out as described above. FIG. 6 shows that the signal is dependent upon the amount of analyte used in the reaction.

Example 5

Figure 7:
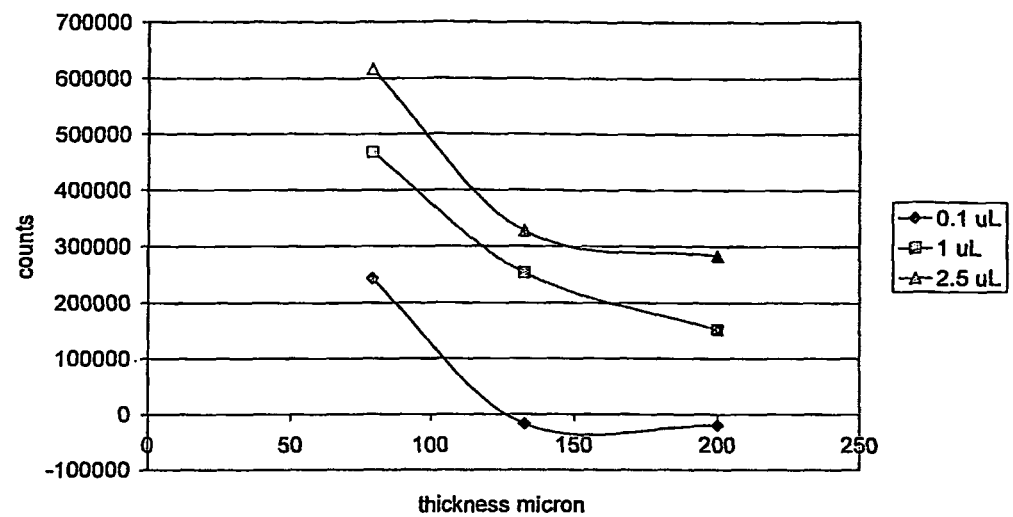
FIG. 7 shows a graph of counts against film thickness demonstrating energy transference through a coloured layer above an uncoloured layer which transfers energy to a piezoelectric film.

In this example, the transducer is coated with a layer of silicone. The signal detected by the transducer depends on both the thickness and the elasticity of the silicone layer. Silicone layers were prepared of varying thickness, with spots of Sudan Black B dye placed atop of the silicone layers by addition of dye solution (in ethanol) by pipette. Three different layer thicknesses (200, 133 and 79 μm) and three different total amounts of dye were used (by adding either 0.1, 1.0 or 2.5 μL of 10 mmol $dm^{-3}$ dye solution), giving a total of nine measurements. FIG. 7 shows that the signal rises significantly as the layer thickness falls (for all three dye quantities) where the correlation delay is 10 ms.

Figure 8:
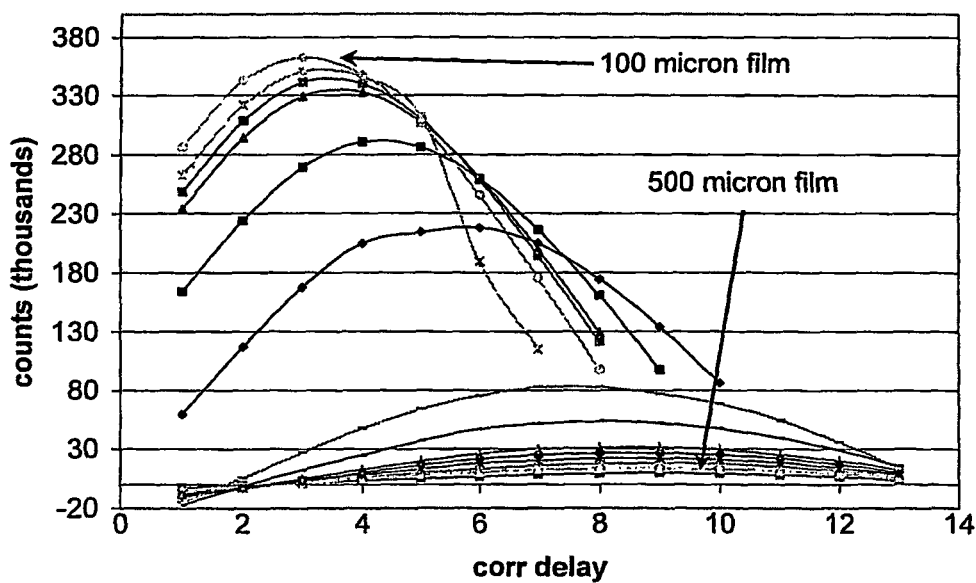
FIG. 8 shows a graph of counts against correlation delay demonstrating energy transference through a coloured layer and an uncoloured layer which transfers energy to a piezoelectric film.

Additionally, the thickness of the intervening silicone layer affects the time taken for the signal to reach a maximum (i.e. the correlation delay). This is illustrated in FIG. 8, where the thickness of an intervening silicone layer between a dye spot and the transducer was varied between 100 and 500 μm. The y axis gives the counts (in thousands), whereas the x axis gives the correlation delay (correlation delay 1=5 ms, 2=10 ms, 3=15 ms, etc). The highest signal is observed for a silicone layer of 100 μm with a correlation delay of 15 ms to reach this maximum. As the thickness of the silicone layer is increased it is observed that the signal falls, and at the same time, the time taken to reach maximum also increases, to 50 ms at a silicone layer thickness of 500 μm.

The invention claimed is:

1. A device for detecting energy generated by non-radiative decay in an analyte or a complex or derivative of the analyte on irradiation with electromagnetic radiation comprising
    a radiation source adapted to generate a series of pulses of electromagnetic radiation,
    a transducer having a pyroelectric or piezoelectric element and electrodes which is capable of transducing the energy generated by the analyte or the complex or derivative of the analyte into an electrical signal,
    at least one reagent proximal to the transducer, the reagent having a binding site capable of binding the analyte or the complex or derivative of the analyte,
    a well for holding a liquid having the analyte or the complex or derivative of the analyte dissolved or suspended therein, the liquid being in contact with the transducer, the analyte or the complex or derivative of the analyte dissolved or suspended in the liquid being at a plurality of positions at different distances from the surface of the transducer, and
    a detector capable of detecting the electrical signal generated by the transducer,
    wherein the detector is configured to detect only the electrical signal generated by the transducer up to a selected time delay between each pulse of electromagnetic radiation from the radiation source and the generation of the electric signal to distinguish the concentration of the analyte or the complex or derivative of the analyte at different distances from the surface of the transducer.

2. A device as claimed in claim 1, wherein the reagent is an antibody and the analyte is an antigen.

3. A device as claimed in claim 2, wherein the complex or derivative of the analyte is a complex with a labelled antibody.

4. A device as claimed in claim 2, wherein the analyte is a labelled antigen and the electrical signal detected by the detector is inversely proportional to the presence of an unlabelled antigen in the sample.

5. A device as claimed in claim 3 or 4, wherein the labelled antibody or antigen is labelled with a label selected from a dye molecule, a gold particle, a coloured-polymer particle, a fluorescent molecule, an enzyme, a red blood cell, a haemoglobin molecule, a magnetic particle and a carbon particle.

6. A device as claimed in claim 1, wherein the reagent is a first nucleic acid and the analyte is a second nucleic acid and the first and second nucleic acids are complementary.

7. A device as claimed in claim 1, wherein the reagent contains avidin or derivatives thereof and the analyte contains biotin or derivatives thereof, or vice versa.

8. A device as claimed in claim 1, wherein the selected time delay is at least 5 milliseconds.

9. A device as claimed in claim 1, wherein the selected time delay is at least 10 milliseconds.

10. A device as claimed in claim 1, wherein the electromagnetic radiation is light.

11. A device as claimed in claim 1, wherein the reagent is adsorbed on to the transducer.

12. A device as claimed in claim 1, further comprising a chamber for storing one or more additional reagents.

13. A device as claimed in claim 12, wherein the additional reagent is a labelled antibody for producing the subsequently formed complex or derivative of the analyte.

14. A device as claimed in claim 1, wherein the frequency of the pulses of electromagnetic radiation is at least 2 Hz.

15. A device as claimed in claim 1, wherein the selected time delay is no greater than 150 milliseconds.

16. A method for detecting an analyte dissolved or suspended in a liquid sample, comprising the steps of:
    exposing the liquid sample, containing the dissolved or suspended analyte, to a transducer having a pyroelectric or piezoelectric element and electrodes which is capable of transducing a change in energy to an electrical signal, the transducer having at least one reagent proximal thereto, the reagent having a binding site which is capable of binding the analyte or a complex or derivative of the analyte, the analyte or the complex or derivative of the analyte being capable of absorbing the electromagnetic radiation generated by the radiation source to generate energy by non-radiative decay, the analyte or the complex or derivative of the analyte dissolved or suspended in the liquid being at a plurality of positions at different distances from the surface of the transducer;
    irradiating the reagent with a series of pulses of electromagnetic radiation,
    transducing the energy generated into an electrical signal;
    detecting only the electrical signal generated by the transducer up to a selected time delay between each pulse of electromagnetic radiation from the radiation source and the generation of the electric signal to distinguish the concentration of the analyte or the complex or derivative of the analyte at different distances from the surface of the transducer, wherein the time delay between each of the pulses of electromagnetic radiation and the generation of the electric signal corresponds to the position of the analyte at any of one or more positions at different distances from the surface of the transducer.

17. A method as claimed in claim 16, wherein the reagent is an antibody and the analyte is an antigen.

18. A method as claimed in claim 17, wherein the complex or derivative of the analyte is a complex with a labelled antibody.

19. A method as claimed in claim 17, wherein the analyte is a labelled antigen and the electrical signal detected by the detector is inversely proportional to the presence of an unlabelled antigen in the sample.

20. A method as claimed in claim 18 or 19, wherein the labelled antibody or antigen is labelled with a label selected from a dye molecule, a gold particle, a coloured-polymer particle, a fluorescent molecule, an enzyme, a red blood cell, a haemoglobin molecule, a magnetic particle and a carbon particle.

21. A method as claimed in claim 16, wherein the reagent is a first nucleic acid and the analyte is a second nucleic acid and the first and second nucleic acids are complementary.

22. A method as claimed in claim 16, wherein the reagent contains avidin or derivatives thereof and the analyte contains biotin or derivatives thereof, or vice versa.

23. A method as claimed in claim 16, wherein the method is carried out without removing the liquid sample from the transducer between the steps of exposing the liquid sample to the transducer and irradiating the reagent.

24. A method as claimed in claim 16, wherein the frequency of the pulses of electromagnetic radiation is at least 2 Hz.

25. A method as claimed in claim 16, wherein the selected time delay is no greater than 150 milliseconds.

26. A device for detecting energy generated by non-radiative decay in an analyte or a complex or derivative of the analyte on irradiation with electromagnetic radiation comprising
- a radiation source configured to generate a series of pulses of electromagnetic radiation,
- a transducer having a pyroelectric or piezoelectric element and electrodes which is capable of transducing the energy generated by the analyte or the complex or derivative of the analyte into an electrical signal,
- at least one reagent proximal to the transducer, the reagent having a binding site capable of binding the analyte or the complex or derivative of the analyte,
- a well configured to hold a liquid bulk sample, which has the analyte or the complex or derivative of the analyte dissolved or suspended therein, in contact with the transducer such that the well contains (i) a portion of the analyte or the complex or derivative of the analyte that is bound to the reagent and (ii) a portion of the analyte or the complex or derivative of the analyte that is not bound to the reagent, and
- a detector capable of detecting the electrical signal generated by the transducer,
- wherein the device is configured to (i) use the radiation source to irradiate the liquid located within the well, (ii) use the detector to monitor the signal generated by the transducer, and (iii) use the time delay between each pulse of electromagnetic radiation and the generation of the electric signal from the transducer to distinguish between a signal arising from non-radiative decay of the analyte or the complex or derivative of the analyte that is proximal to the transducer and the signal arising from non-radiative decay of the analyte or the complex or derivative of the analyte located elsewhere within the bulk sample.

27. A device for detecting energy generated by non-radiative decay in an analyte or a complex or derivative of the analyte on irradiation with electromagnetic radiation comprising
- a radiation source adapted to generate a series of pulses of electromagnetic radiation,
- a transducer having a pyroelectric or piezoelectric element and electrodes which is capable of transducing the energy generated by the analyte or the complex or derivative of the analyte into an electrical signal,
- at least one reagent proximal to the transducer, the reagent having a binding site capable of binding the analyte or the complex or derivative of the analyte,
- a well for holding a liquid having the analyte or the complex or derivative of the analyte dissolved or suspended therein, the liquid being in contact with the transducer, the analyte or the complex or derivative of the analyte dissolved or suspended in the liquid comprising a portion that is proximal to the transducer and a portion that is not proximal to the transducer, and
- a detector capable of detecting the electrical signal generated by the transducer,
- wherein the detector is configured to determine the time delay between each pulse of the electromagnetic radiation from the radiation source and the generation the electrical signal from the transducer, and
- wherein the detector is configured to detect the electrical signal generated by the transducer only up to a selected time delay to distinguish between a portion of the analyte or the complex or derivative of the analyte that is proximal to the transducer and a portion of the analyte or the complex or derivative of the analyte that is not proximal to the transducer.

28. A device for detecting energy generated by non-radiative decay in an analyte or a complex or derivative of the analyte on irradiation with electromagnetic radiation comprising
- a radiation source adapted to generate a series of pulses of electromagnetic radiation,
- a transducer having a pyroelectric or piezoelectric element and electrodes which is capable of transducing the energy generated by the analyte or the complex or derivative of the analyte into an electrical signal,
- at least one reagent proximal to the transducer, the reagent having a binding site capable of binding the analyte or the complex or derivative of the analyte,
- a well for holding a liquid having the analyte or the complex or derivative of the analyte dissolved or suspended therein, the liquid being in contact with the transducer, the analyte or the complex or derivative of the analyte dissolved or suspended in the liquid being at a plurality of positions at different distances from the surface of the transducer, and
- a detector capable of detecting the electrical signal generated by the transducer,
- wherein the detector is configured to determine the time delay between each pulse of the electromagnetic radiation from the radiation source and the generation the electrical signal from the transducer, and
- wherein the detector is configured to detect the electrical signal generated by the transducer only up to a selected time delay to determine the concentration of the analyte or the complex or derivative of the analyte at a predetermined distance from the surface of the transducer.

29. A device for detecting energy generated by non-radiative decay in an analyte or a complex or derivative of the analyte on irradiation with electromagnetic radiation comprising
- a radiation source adapted to generate a series of pulses of electromagnetic radiation,
- a transducer having a pyroelectric or piezoelectric element and electrodes which is capable of transducing the energy generated by the analyte or the complex or derivative of the analyte into an electrical signal,
- at least one reagent proximal to the transducer, the reagent having a binding site capable of binding the analyte or the complex or derivative of the analyte,
- a well for holding a liquid having the analyte or the complex or derivative of the analyte dissolved or suspended therein, the liquid being in contact with the transducer, the analyte or the complex or derivative of the analyte dissolved or suspended in the liquid being at a plurality of positions at different distances from the surface of the transducer, and
- a detector capable of detecting the electrical signal generated by the transducer,
- wherein the detector is configured to determine the time delay between each pulse of the electromagnetic radiation from the radiation source and the generation the electrical signal from the transducer, and
- wherein the detector is configured to detect the electrical signal generated by the transducer only up to a selected time delay to determine the concentration of the analyte or the complex or derivative of the analyte at no more than 500 µm from the surface of the transducer.

30. A device for detecting energy generated by non-radiative decay in an analyte or a complex or derivative of the analyte on irradiation with electromagnetic radiation comprising
- a radiation source configured to generate a series of pulses of electromagnetic radiation,
- a transducer having a pyroelectric or piezoelectric element and electrodes which is capable of transducing the energy generated by the analyte or the complex or derivative of the analyte into an electrical signal,
- at least one reagent proximal to the transducer, the reagent having a binding site capable of binding the analyte or the complex or derivative of the analyte,
- a well configured to hold a liquid bulk sample, which has the analyte or the complex or derivative of the analyte dissolved or suspended therein, in contact with the transducer such that the well contains (i) a portion of the analyte or the complex or derivative of the analyte that is bound to the reagent and (ii) a portion of the analyte or the complex or derivative of the analyte that is not bound to the reagent, and
- a detector capable of detecting the electrical signal generated by the transducer,
- wherein the detector is configured to measure the electrical signal generated by the transducer only up to a selected time delay between each pulse of electromagnetic radiation from the radiation source and the generation of the electric signal, and the selected time delay is such that only the electrical signal corresponding to energy generated by the portion of the analyte or the complex or derivative of the analyte that is bound to the reagent is measured.

\* \* \* \* \*